(12) United States Patent
Lisec

(10) Patent No.: US 8,029,527 B2
(45) Date of Patent: Oct. 4, 2011

(54) DEVICE FOR LOCAL PUNCTURING OF SKIN

(75) Inventor: Walter Lisec, Berlin (DE)

(73) Assignee: MT Derm GmbH, Berlin (DE)

( * ) Notice: Subject to any disclaimer, the term of this patent is extended or adjusted under 35 U.S.C. 154(b) by 316 days.

(21) Appl. No.: 11/040,107

(22) Filed: Jan. 24, 2005

(65) Prior Publication Data

US 2006/0020283 A1     Jan. 26, 2006

(30) Foreign Application Priority Data

Jul. 21, 2004 (EP) ..................................... 04017195

(51) Int. Cl.
    *A61B 17/34*     (2006.01)
(52) U.S. Cl. ...................................................... 606/185
(58) Field of Classification Search .................. 606/185, 606/186; 81/9.22
See application file for complete search history.

(56) References Cited

U.S. PATENT DOCUMENTS

| | | | |
|---|---|---|---|
| 5,472,449 A | 12/1995 | Chou | |
| 5,591,188 A * | 1/1997 | Waisman | 606/182 |
| 5,616,132 A * | 4/1997 | Newman | 604/185 |
| 6,345,553 B1 | 2/2002 | Adler et al. | |
| 6,505,530 B2 * | 1/2003 | Adler et al. | 81/9.22 |
| 6,588,301 B1 | 7/2003 | Chanet et al. | |

FOREIGN PATENT DOCUMENTS

DE      299 19 199 U      1/2000

* cited by examiner

*Primary Examiner* — Elizabeth Houston
*Assistant Examiner* — Julie A Szpira
(74) *Attorney, Agent, or Firm* — Smith Patent Office

(57) ABSTRACT

A device for locally puncturing skin is disclosed, especially for applying permanent make-up or a tattoo, comprising a housing, a needle guided in the housing for movement between extended and retracted positions, and a diaphragm made of an elastically extensible material and dividing a front-end space at a front surface of the diaphragm from a rear-end space at a back surface of the diaphragm in the housing. A coupling mechanism firmly couples the needle and the diaphragm for backward movement of the needle in the direction of the retracted position, a return force generated by the diaphragm for moving the needle back in the direction of the retracted position being introduced into the needle shaft.

17 Claims, 2 Drawing Sheets

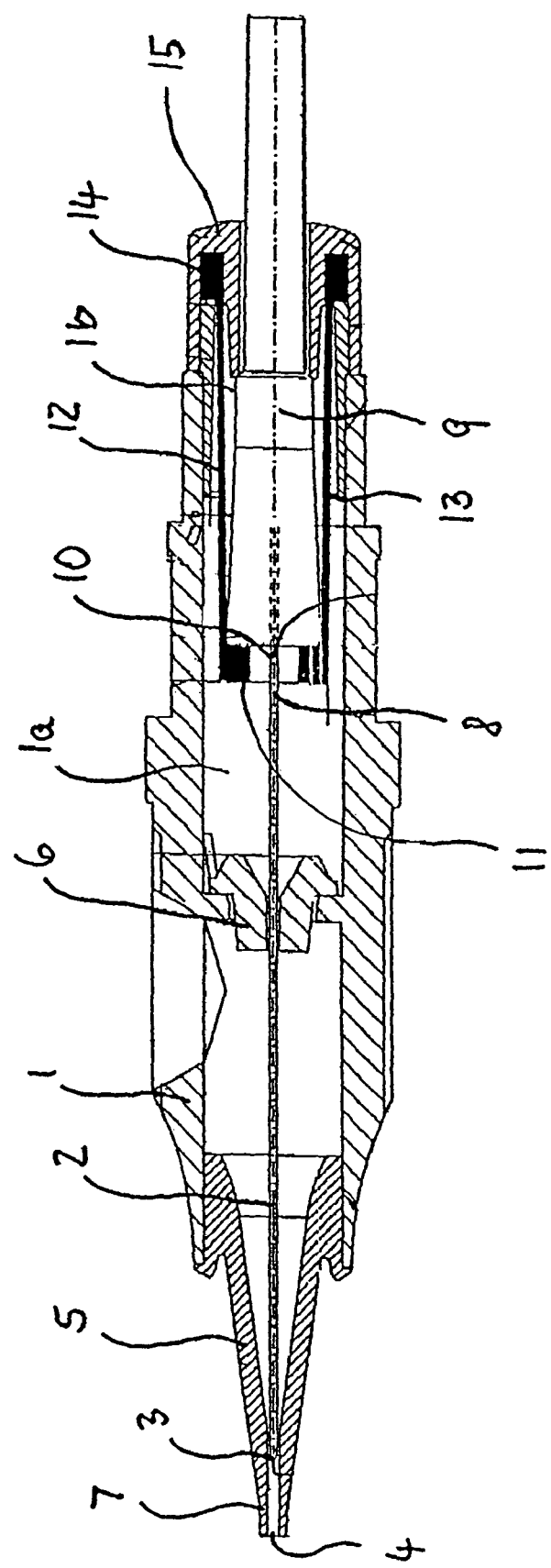

DEVICE FOR LOCAL PUNCTURING OF SKIN

BACKGROUND OF THE INVENTION

1. Field of the Invention

The invention relates to a device for locally puncturing skin, especially for applying permanent make-up or a tattoo.

2. Discussion of the Related Art

A device of the kind in question is known, for instance, from U.S. Pat. No. 6,505,530 B2. With this known device a needle is guided in a housing so as to be movable between an extended position in which the tip of the needle lies outside of an aperture in the housing and a retracted position in which the tip of the needle is located inside the housing. By repetitive forward and backward movements, shifting the needle between the extended and retracted positions, the needle repeatedly penetrates the skin and is subsequently withdrawn again from the same. A medium for application in liquid form thus may be introduced into the skin. When the known device is used for applying permanent make-up or for tattooing coloring matter is introduced into the skin. The coloring matter either may be applied by immersing a tip of the housing in a reservoir of coloring matter whereby the coloring matter will become distributed along the needle, perhaps all the way into the housing. Operating the device will allow the coloring matter to get into the punctured skin region. Alternatively, or in addition, a container filled with coloring mater may be disposed at the housing of the device to assure replenishing of coloring matter in the interior of the housing and in contact with the reciprocating needle.

In the known device, the needle is driven forward by a drive means which includes a motor. The housing together with the needle guided by it may be implemented as a separate module adapted to be coupled to and detached from the drive means. But the housing and the guided needle and the drive means also may be integrated in a single device. Likewise known are devices which allow the needle to be removed from the housing.

The housing of the known device includes a diaphragm made of an elastically extensible material to prevent liquid, both coloring matter and any body fluid released when the skin is punctured, from reaching the zone where the drive means is coupled or even getting into the drive means itself. The diaphragm separates a front-end space in the housing at a front surface of the diaphragm from a rear-end space in the housing at a back side of the diaphragm. The diaphragm establishes a tight seal between the two spaces inside the housing. The above mentioned U.S. Pat. No. 6,505,530 B2 describes embodiments with the needle extending through a breakthrough in the diaphragm and being surrounded in the region of the breakthrough by a sealing lip. When being shifted between the extended and retracted positions, the needle thus slips in the breakthrough and the sealing lip slides on the needle. Operating the known device for locally puncturing skin causes the needle to move from the retracted position into the extended position by the propelling force of a drive means. The return movement of the needle from the extended position back into the retracted position is accomplished by the force of a helical spring arranged in the housing. This spring force is introduced into the needle through the shaft of the needle.

Also known are devices for local puncturing of skin, especially for applying permanent make-up or a tattoo with which the tip of the needle is not received in the surrounding housing when the needle itself is in its retracted position. Instead the tip still projects outwardly.

SUMMARY OF THE INVENTION

It is an object of the invention to provide an improved device, having a simplified mechanical structure, for local puncturing of skin, especially for applying permanent make-up or a tattoo.

This object is met, in accordance with the invention, with a device for local puncturing of skin to apply permanent make-up or a tattoo where a coupling mechanism firmly couples the needle and the diaphragm for backward movement of the needle in the direction of the retracted position, and a return force is generated by the diaphragm to move the needle backwards into the retracted position being introduced into the needle.

It is an advantage achieved by the invention over the prior art that it can do without the spring provided in known devices for providing the return force to move the needle back in the direction of the retracted position. Instead, the return force is provided by the diaphragm when the latter is extended. Apart from the separating function inside the housing, the diaphragm thus fulfills another function, namely that of returning the needle from its extended position. To this end, the needle and the diaphragm are firmly interconnected by the coupling mechanism. This means that the needle and a coupling portion of the diaphragm to which the needle is coupled are fixed in position with respect to each other during the retraction of the diaphragm. The needle thus is secured to the diaphragm especially against slippage. This is in contrast to the known device which provides slidable support of the needle or the shaft of the needle in a breakthrough of the diaphragm. Consequently, not only the number of parts is reduced that must be assembled to manufacture the device but, at the same time, the structure is simplified.

Another advantage obtained, in comparison with the known device in which the needle is reciprocated with the help of a spring, resides in the fact that the operation of the device causes less noise.

In a preferred embodiment of the invention, a simple mechanical way of coupling the needle to the diaphragm so as to introduce the return force into the needle is realized in that the needle is formed with a shaft and the return force generated by the diaphragm is introduced through the shaft into the needle. As far as the structural implementation of the needle shaft is concerned, the shaft is a member which can be optimized independently and is connected rigidly to the needle.

In accordance with a modification of the invention the coupling mechanism includes a mounting portion formed at the diaphragm to retain the needle at the front surface of the diaphragm, one end of the needle being received in the mounting portion.

Alternatively, the firm coupling between the diaphragm and the needle may be obtained by way of a drive member which, for instance, may be an extension forming part of the drive mechanism by which the propelling force for advancing the needle is transmitted to the needle. This couples the drive member and the diaphragm together, the needle being rigidly connected to the drive member to carry out the return movements. This connection, optionally, may be established through intermission of the needle shaft. The return force generated by the diaphragm and introduced into the drive member by virtue of the coupling moves back the drive member which takes along the needle.

In a convenient embodiment of the invention the front-end space at the front surface of the diaphragm and the rear-end space at the back surface of the diaphragm are separated in fluid tight fashion by the diaphragm. Thus it is assured that neither the medium introduced through the local punctures of the skin nor any body fluid will leave the zone in which the needle is guided in the housing and reach the back of the diaphragm where the drive mechanism is coupled. The rear-end space might be formed in the drive mechanism if the diaphragm is designed to be the rear closure of the housing.

The diaphragm comprises extensible portions which are formed essentially in longitudinal direction of the needle in a non-extended basic configuration of the diaphragm. With this embodiment the return force for moving back the needle in the direction of the retracted position is generated essentially by virtue of the extensible portions in longitudinal direction of the needle. Thus the return forces substantially act in longitudinal direction of the needle, whereby the efficiency of their action is improved.

Portions of the diaphragm which are extensible in longitudinal direction of the needle are obtained, with a preferred embodiment of the invention, by designing a cross section of the diaphragm to be U-shaped or V-shaped in longitudinal direction.

It is preferred that the diaphragm should be mounted detachably on the housing as that facilitates making use of different diaphragms and/or replacing them when worn.

The housing may be designed as a module for releasable coupling to a drive module. In this manner devices with different needles can be used with the same drive module. Moreover, it is possible to replace worn devices together with the needle guided inside the housing when they are no longer useful. Especially preferred in this context is a module of a housing designed as a disposable module.

The advantages described above of the device for local puncturing of the skin are obtained no matter whether the device is used for applying permanent make-up or a tattoo or whether it is employed to administer an active substance through the skin, for example a medical substance or a cosmetic agent.

BRIEF DESCRIPTION OF THE DRAWINGS

The invention will be described further, by way of example, with reference to the accompanying drawing, in which:

FIG. 1 is a cross sectional elevation of a device for local puncturing of skin, comprising a housing and a needle guided in the housing.

DETAILED DESCRIPTION OF THE PREFERRED EMBODIMENTS

Figure 2A:
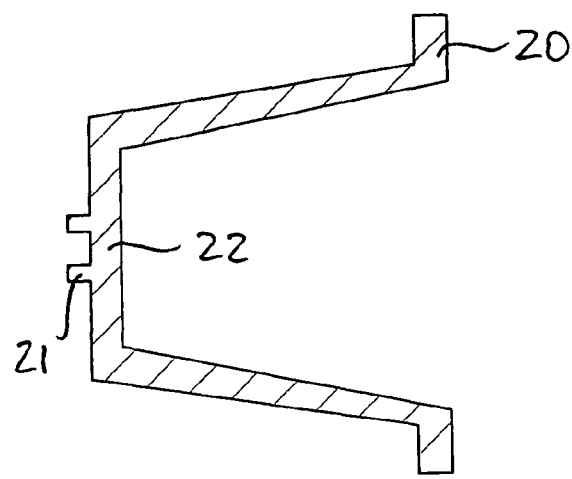
FIGS. 2A to 2C are cross sections of diaphragms to be used in the device shown in FIG. 1.

FIG. 1 illustrates a device for local puncturing of skin, especially for applying permanent make-up or a tattoo or for administration of an active substance. The device comprises a housing 1 in which a needle 2 is guided so as to be movable between a retracted position, shown in FIG. 1, and an extended position at which a tip 3 of the needle 2 is located outside of an aperture 4 at a tip 5 of the housing 1. Likewise conceivable are embodiments with which the tip 3 of the needle 2, even in retracted position, still lies outside of the housing 1, albeit in a position which is displaced to the rear.

When the needle 2 is being moved into the extended position, in the embodiment shown, so that the tip 3 of the needle 2 exits from the aperture 4, the skin is punctured locally and a medium can enter into the skin. Thereafter, the needle 2 is moved back into the housing 1 and then extended once again. These reciprocating motions of the needle 2 are repeated at high frequency. The needle 2 is guided during these movements in a bushing 6 which acts as a needle guide together with the front end 7 of the tip 5 of the housing 1.

At its rear end 8 the needle 2 is formed with a shaft 9. The needle 2 is arranged in a breakthrough 10 of a central portion 11 of a diaphragm 12. The diaphragm 12 is made of an elastically extensible material, such as rubber or plastic. Since the breakthrough 10 has a somewhat smaller cross section than the cross section of the needle shaft 9 the needle shaft 9 will get clamped in the breakthrough 10 upon introduction into the same, whereby the sealing effect is enhanced. In an alternative embodiment (not shown) the needle 2 itself can be clamped in the breakthrough 10, if the breakthrough 10 has a somewhat smaller cross section than the cross section of the needle 2.

The diaphragm 12 separates a front-end interior space 1a at the front surface of the diaphragm from a rear-end interior space 1b in the housing 1. The separation by means of the diaphragm 12 preferably is fluid tight so that the liquid medium to be introduced into the skin and/or the body fluid exiting when the skin is punctured will not get from the front-end interior space 1a into the rear-end interior space 1b. In the embodiment shown in FIG. 1 the rear-end interior space 1b is defined in the housing 1. However, it may also be provided that the diaphragm 12 terminates the housing 1 so that the space at the back of the diaphragm 12, being the rear-end interior space 1b in the embodiment illustrated, would be outside of the housing 1, being defined in a drive mechanism (not shown) which is to be coupled to the housing.

During operation of the device for puncturing skin, a drive mechanism which, for example, may be screwed or plugged to the housing generates a driving force to move the needle 2 into the extended position, this driving force being introduced through the shaft 9 into the needle 2. The shaft 9 presses against the back of the central portion 11 of the diaphragm 12. This results in elongating the diaphragm 12, especially in the area of a lateral portion 13 which extends substantially in a longitudinal direction of the needle 2. Due to this stretching of the diaphragm 12 towards the front-end interior space 1a, a return force is built up by the diaphragm 12 and introduced through the central portion 11 into the shaft 9 of the needle and then into the needle 2. As a result, the needle 2 returns into the retracted position illustrated in FIG. 1 when the driving force propelling the needle 2 forwards no longer acts on the shaft 9 of the needle. During the return movement of the needle 2 the central portion 11 presses against the shaft 9, whereby firm coupling is established between the two to make sure that the central portion 11 and the shaft 9 of the needle are coupled together so that they can jointly carry out the return movement, being firmly fixed in their relative mutual positions. The needle 2 thus is not brought back into its retracted position due to the backward movement of a coupling member of the drive mechanism but instead by the return force generated by the diaphragm 12. This is an essential difference over known devices with which the needle or the shaft of the needle is pulled back by the coupling member of the drive mechanism.

Firm coupling between the needle 2 and the diaphragm 12 may be obtained, alternatively or in addition to the configuration described above, by forming a depression in the circumference of the needle 2 to be engaged by a projection at the diaphragm 12. In this manner, too, a tightly sealed separation as well as firm coupling are obtained.

The sealing effect between the needle 2 and the breakthrough 10 in the central portion 11 of the diaphragm 12 can be optimized by making the diaphragm 12 thicker in the central portion 11 than in the lateral portion 13. At its outer periphery the diaphragm 12 comprises a fixing portion 14 secured to the housing 1 to retain the diaphragm 12, for example by a clamping effect. The diaphragm 12 may be taken out of the housing 1 once a terminal end part 15 has been removed from the housing 1.

Figure 2B:
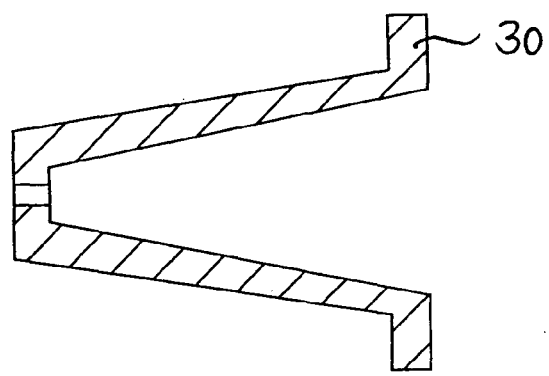
Figure 2C:
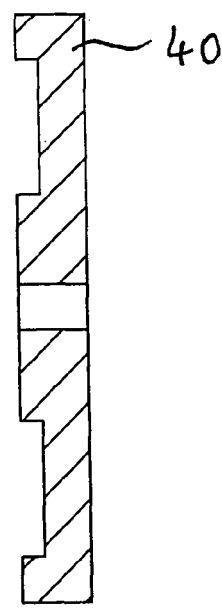

FIGS. 2A to 2C illustrate further embodiments of diaphragms 20, 30, 40 which may be used as the diaphragm 12 in the device according to FIG. 1. In particular, the cross section of the diaphragm may be U-shaped or V-shaped. FIG. 2A shows an embodiment with which, instead of the breakthrough 10 of the diaphragm 12 for reception of the needle 2 as in FIG. 1, there is a front-end mounting portion 21 into which the needle 2 or the shaft 9 of the needle can be inserted so as to couple the needle 2 firmly to the diaphragm 20. Hereby the needle 2 will also be moved back into the retracted position when the diaphragm 12 retracts, following its elongation. With this embodiment the driving force is not introduced into the needle 2 through direct contact between the needle 2/shaft 9 of the needle 2 and the drive mechanism but instead through intermission of a diaphragm portion 22 which has a damping effect, acting as a kind of coupling element.

The features disclosed in the specification above, in the claims and drawing may be significant for implementing the invention in its various embodiments, both individually and in any combination.

This application is based on European Patent Application No. 04017195.1 filed on Jul. 21, 2004, the contents of which are incorporated hereinto by reference.

What is claimed is:

1. A disposable/detachable device for connecting to and detaching from a drive module, for local puncturing of skin to apply permanent make-up or a tattoo, comprising:
  a needle having a stepped surface thereon;
  a housing having a first end toward a tip of the needle and a second end closer to the drive module, the needle being guided in the housing for movement between extended and retracted positions;
  a diaphragm made of an elastically extensible material having a central portion of the diaphragm forming a central opening disposed on the stepped surface of the needle, a wall portion extending from the central portion toward the second end of the housing; and a fixing portion formed at an end of the wall portion of the diaphragm;
  a terminal end part which is attached to the second end of the housing, and wherein the terminal end part holds the fixing portion of the diaphragm in the second end of the housing; and
  wherein the diaphragm divides a space in the housing into a front-end space toward the first end of the housing and a rear-end space toward the second end of the housing;
  wherein the stepped surface of the needle contacts and supports a part of the central portion of the diaphragm and the central opening of the diaphragm firmly couples the needle and the diaphragm for backward movement of the needle in the direction of the retracted position.

2. The device as claimed in claim 1, wherein the needle includes a needle shaft and the return force generated by the diaphragm is introduced into the needle through the needle shaft.

3. The device as claimed in claim 1, wherein the front-end space and the rear-end space are separated in fluid tight fashion by the diaphragm.

4. The device as claimed in claim 1, wherein in the retracted position, a cross section of the diaphragm in a direction between the first end and the second end of the housing is U-shaped or V-shaped.

5. The device as claimed in claim 1, wherein the diaphragm is releasably mounted in the housing.

6. The device as claimed in claim 1, wherein the housing is devised as a module for releasable coupling to the drive module.

7. The device as claimed in claim 6, wherein the module is a disposable module.

8. The device as claimed in claim 1, wherein the device is used for applying permanent make-up or a tattoo to skin.

9. The device as claimed in claim 1, wherein the device is used for applying an active substance through the skin.

10. The device as claimed in claim 1, wherein when the terminal end part is removed from the housing, the diaphragm is capable of being taken out from the housing.

11. A device as claimed in claim 1, wherein the needle includes a needle shaft; a portion of the needle is disposed in one end of the needle shaft; and the stepped surface is formed in the needle shaft.

12. A device for local puncturing of skin to apply permanent make-up or a tattoo, comprising:
  a housing having a first end toward a tip of a needle and a second end disposed farther from the tip of the needle than the first end, the needle being guided in the housing for movement between extended and retracted positions;
  a diaphragm made of an elastically extensible material having a central portion of the diaphragm without any openings therein and a wall portion extending from the central portion toward the second end of the housing; and
  wherein the diaphragm divides a space in the housing into a front-end space toward the first end of the housing and a rear-end space toward the second end of the housing;
  wherein the diaphragm includes a mounting portion formed on a front surface of the central portion, which is toward the first end of the housing, for retaining the needle, and a rear end of the needle directly contacts the central portion and is disposed in the mounting portion to firmly couple the needle and the diaphragm for backward movement of the needle in the direction of the retracted position.

13. The device as claimed in claim 12, further comprising a terminal end part which is attached to the second end of the housing, and is removable from the housing, and wherein the terminal end part holds a fixing portion formed at the end of the wall portion of the diaphragm.

14. The device as claimed in claim 13, wherein when the terminal end part is removed from the housing, the diaphragm is capable of being taken out from the housing.

15. A device for local puncturing of skin to apply permanent make-up or a tattoo, comprising:
  a housing having a first end toward a tip of a needle and a second end farther from the tip of the needle than the first end, the needle being guided in the housing for movement between extended and retracted positions;
  a needle shaft connected to the needle and the needle shaft having a stepped surface thereon;
  a diaphragm made of an elastically extensible material having a central portion of the diaphragm forming a central opening disposed around the needle and a wall portion extending from the central portion toward the second end of the housing;

wherein the stepped surface of the needle shaft contacts and supports a portion of the central portion of the diaphragm; and wherein the central opening of the diaphragm firmly couples the diaphragm and at least one of the needle and the needle shaft for backward movement of the needle and the needle shaft in the direction of the retracted position.

16. The device as claimed in claim 15, further comprising a terminal end part which is attached to the second end of the housing, and is removable from the housing, and wherein the terminal end part holds a fixing portion formed at the end of the wall portion of the diaphragm.

17. The device as claimed in claim 16, wherein when the terminal end part is removed from the housing, the diaphragm is capable of being taken out from the housing.

* * * * *